(12) United States Patent
Kaushik et al.

(10) Patent No.: US 7,939,680 B2
(45) Date of Patent: May 10, 2011

(54) PROCESS FOR THE PREPARATION OF ESCITALOPRAM

(75) Inventors: Vipin Kumar Kaushik, Hyderabad (IN); Umar Khan Mohammed, Hyderabad (IN); Sivakumaran Meenakshisunderam, Hyderabad (IN)

(73) Assignee: Aurobindo Pharma Ltd., Hyderabad (IN)

( * ) Notice: Subject to any disclaimer, the term of this patent is extended or adjusted under 35 U.S.C. 154(b) by 448 days.

(21) Appl. No.: 11/989,621

(22) PCT Filed: Jul. 20, 2006

(86) PCT No.: PCT/IB2006/002050
§ 371 (c)(1),
(2), (4) Date: Jan. 26, 2008

(87) PCT Pub. No.: WO2007/012954
PCT Pub. Date: Feb. 1, 2007

(65) Prior Publication Data
US 2009/0099375 A1    Apr. 16, 2009

(30) Foreign Application Priority Data
Jul. 27, 2005  (IN) .......................... 1014/CHE/2005

(51) Int. Cl.
*C07D 307/00* (2006.01)

(52) U.S. Cl. .................................................... 549/467
(58) Field of Classification Search ............... 549/467
See application file for complete search history.

(56) References Cited

U.S. PATENT DOCUMENTS

| 4,650,884 A | * | 3/1987 | Bogeso | 549/467 |
|---|---|---|---|---|
| 4,943,590 A | * | 7/1990 | Boegesoe et al. | 514/469 |
| RE34,712 E | | 8/1994 | Boegesoe et al. | |
| 7,390,913 B2 | | 6/2008 | Petersen et al. | |
| 7,435,838 B2 | | 10/2008 | Mei et al. | |
| 2005/0154051 A1 | | 7/2005 | Ahmadian et al. | |
| 2007/0117992 A1 | | 5/2007 | Mei et al. | |
| 2007/0270599 A1 | | 11/2007 | Cotticelli et al. | |
| 2008/0177096 A1 | | 7/2008 | Nagarajan et al. | |

FOREIGN PATENT DOCUMENTS

| WO | WO 2006/025071 A1 | 3/2006 |
|---|---|---|
| WO | WO 2008/059514 A2 | 5/2008 |
| WO | WO 2008/142379 A2 | 11/2008 |
| WO | WO 2009/033488 A1 | 3/2009 |

* cited by examiner

*Primary Examiner* — Nizal S Chandrakumar
(74) *Attorney, Agent, or Firm* — Jay R. Akhave

(57) ABSTRACT

The present invention relates to an improved process for the preparation of Escitalopram of the Formula (I), which comprises, isolation of Diol compound as an oxalate salt, resolution of Diol compound and cyclization of resolved compound of Formula (VII). The present invention provides a process to obtain pure Diol compound by preparing its Oxalate salt, which is useful for resolution of enantiomers.

8 Claims, No Drawings

PROCESS FOR THE PREPARATION OF ESCITALOPRAM

FIELD OF THE INVENTION

The present invention relates to an industrially advantageous process for the preparation of pure Escitalopram, (S)-(+)-1-[3-(dimethylamino)propyl]-1-(4-fluorophenyl)-1,3-dihydro-5-isobenzofurancarbonitrile of Formula I, and its pharmaceutical acceptable salts.

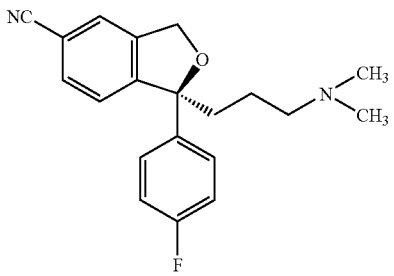

I

BACKGROUND OF THE INVENTION

Escitalopram is the S-enantiomer of an antidepressant drug Citalopram of Formula II.

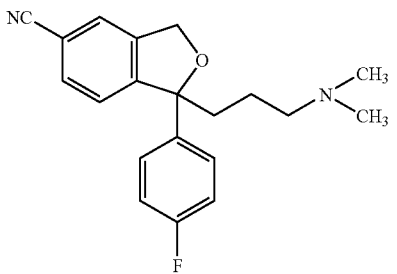

II

Citalopram is a well known antidepressant drug that has now been in the market for several years and is chemically known as 1-[3-(dimethylamino)propyl]-1-(4-fluorophenyl)-1,3-dihydroisobenzofuran-5-carbonitrile.

Citalopram is a selective centrally acting serotonin (5-HT) reuptake inhibitor. Citalopram was first disclosed in DE 2,657,013, corresponding to U.S. Pat. No. 4,136,193.

The antidepressant activity of Citalopram has been reported in several publications, e.g. *J. Hyttel, Prog. Neuro-Psychophannacol & Biol. Psychiat.*, 1982, 6, 277-295 and *A. Grravem, Acta Psychiatr. Scand.*, 1987, 75, 478-486.

The process for the preparation of antidepressant Citalopram and its pharmaceutical properties were first disclosed in U.S. Pat. No. 4,136,193. Citalopram was produced from the corresponding 5-bromo derivative by reaction with cuprous cyanide. Further, variants of this method are disclosed in PCT Publications, WO 00/13648 and WO 00/11926 wherein the exchange of 5-halogen or 5-CF$_3$—(CF$_2$)$_n$—SO$_2$—O— with cyano group is achieved with cyanide source such as KCN, NaCN or (R'$_4$N)CN, where R'$_4$ indicates four groups which may be same or different and are selected from hydrogen and straight chain or branched C$_{1-6}$ alkane, in presence of palladium or nickel catalyst.

The diol, 4-[4-(dimethylamino)-1-(4'-fluorophenyl)-1-hydroxybutyl]-3-(hydroxymethyl)-benzonitrile (VI), and its use as an intermediate in the preparation of Citalopram has been disclosed in U.S. Pat. No. 4,650,884. In this reference, 5-cyanophthalide of Formula III is reacted successively with p-fluorophenylmagnesium bromide and 3-(N,N-dimethylamino)propylmagnesium chloride to get the compound of the Formula VI and its further conversion to Citalopram base is achieved by reaction with 70% sulfuric acid.

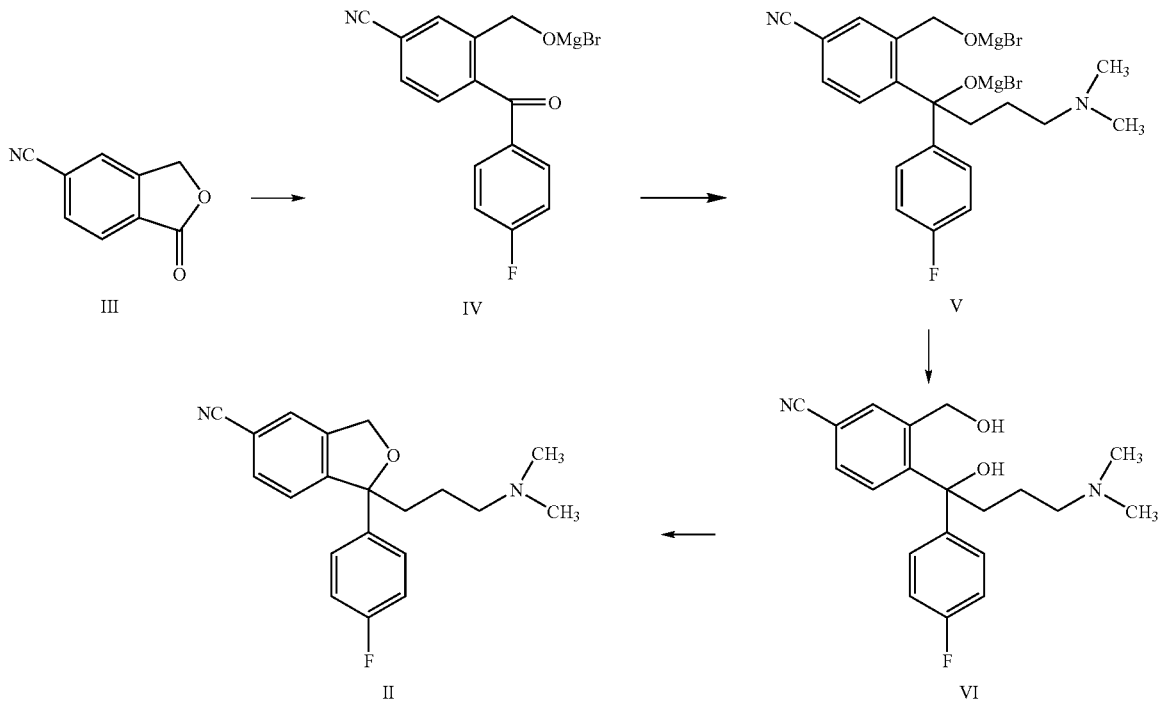

The S-enantiomer (Escitalopram) of the Formula I and the antidepressant effect of said enantiomer is disclosed in U.S. Pat. No. 4,943,590, wherein use of Escitalopram for the treatment of neurotic disorders has been described. WO 02/087566 describes the use of Escitalopram for treating depressive patients who have failed to respond to conventional SSRIs.

Escitalopram has now been developed as an antidepressant and hence a need for a commercially feasible method to produce Escitalopram has emerged.

Process for the preparation of Escitalopram was first disclosed in U.S. Pat. No. 4,943,590. According to this patent reference, attempts to resolve Citalopram enantiomers to produce Escitalopram were not successful. Therefore, resolution of enantiomers of the diol compound (VI) with optically active selective precipitant, Di-p-toluoyl-D-tartaric acid, has been carried out to obtain (S)-Enantiomer of Diol prior to ring closure in a stereospecific manner to obtain Escitalopram (I) as shown below:

The resolution of enantiomers requires high purity of Diol compound (VI) to selectively precipitate out (S)-Diol hemi Di-p-toluoyl-D-tartaric acid salt having substantially high chiral purity. The Diol compound (VI), obtained as described in U.S. Pat. No. 4,650,884, is not sufficiently pure and extensive purification steps have been described in this reference, which involve repeated charcoal and silica gel treatment of the Diol compound. Further, purification of Diol compound has been carried out by preparing hydrobromide salt and subsequently by crystallization, first from water and thereafter from 2-propanol/ethanol.

The present invention provides a simple and economical process for the purification of Diol compound (VI), which can be used for commercial production of Escitalopram.

OBJECTIVE OF THE INVENTION

The main objective of the invention is to provide an improved process for the preparation of highly pure Escitalopram in high yield.

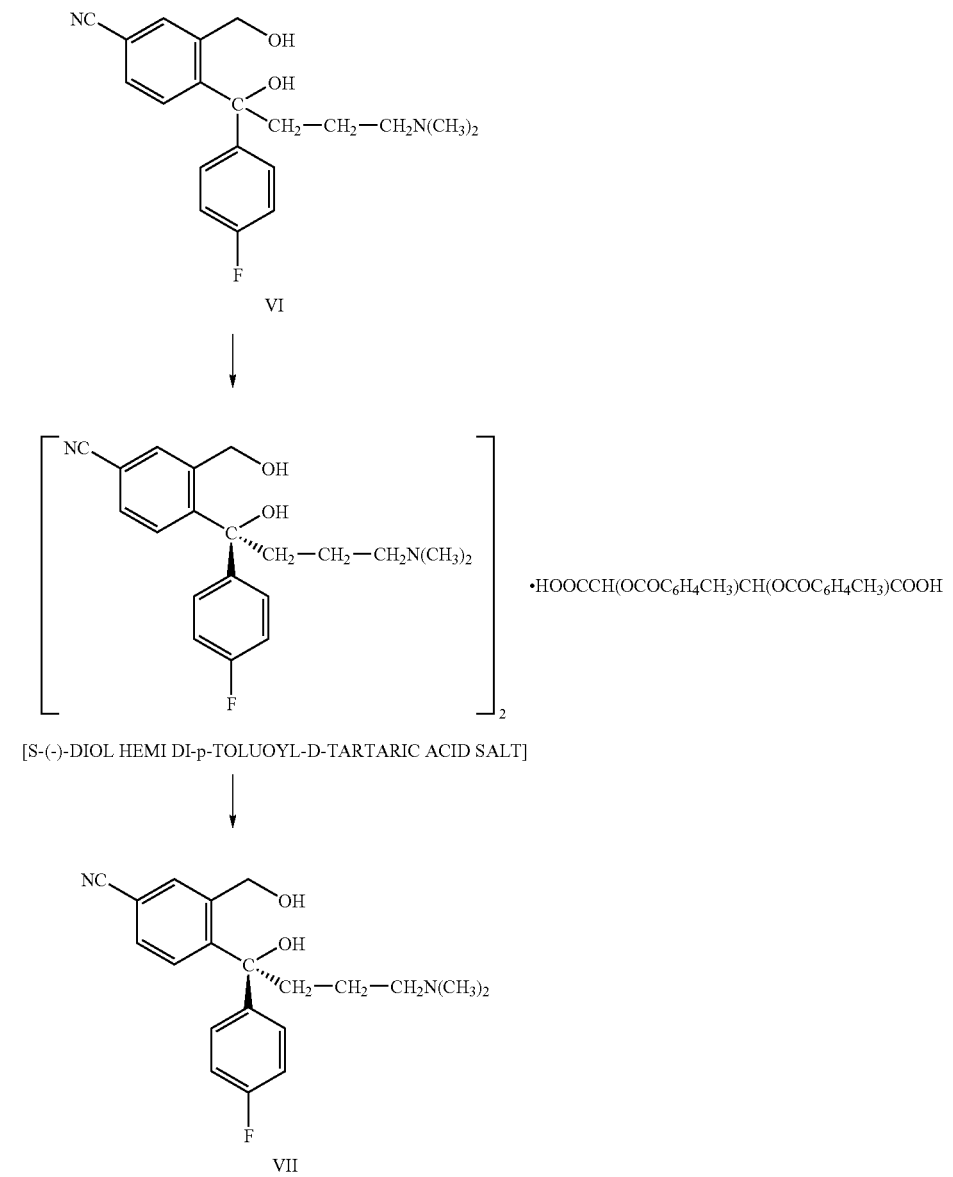

SUMMARY OF THE INVENTION

According to the present invention, a process is provided for the manufacture of highly pure (S)-(+)-1-(4'-fluorophenyl)-1-(3-dimethylaminopropyl)-5-phthalanecarbonitrile of Formula I and its oxalate salt (Escitalopram oxalate), which comprises:

(i) reacting the Diol compound (VI),

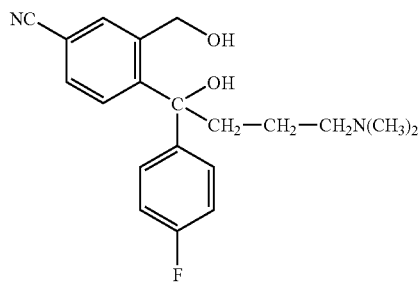

with oxalic acid in an organic solvent to get crystalline oxalate salt of (±)-4-[4-(dimethylamino)-1-(4-fluorophenyl)-1-hydroxybutyl]-3-(hydroxymethyl) benzonitrile [(±)-Diol oxalate] (VIa),

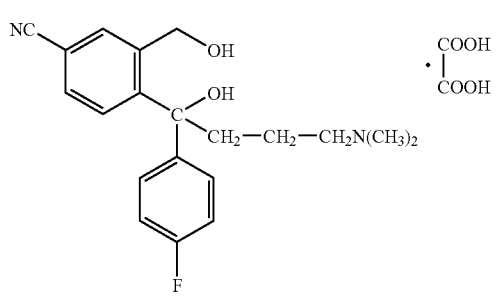

(ii) isolating the crystalline Citalopram diol oxalate (VIa) by filtration and neutralizing the oxalate salt to get pure diol compound (VI),
(iii) separating the enantiomers from the pure Diol compound (VI) with an optically active acid precipitant to obtain (S)-(−)-4-[4-(dimethylamino)-1-(4-fluorophenyl)-1-hydroxybutyl]-3-(hydroxymethyl)benzonitrile (VII),

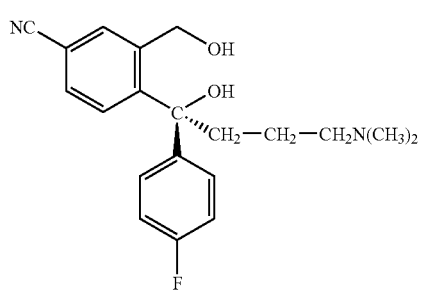

(iv) cyclizing the (S)-(−)-Diol (VII) in an organic solvent in the presence of sulfonyl halide and a base to produce Escitalopram (I).

DETAILED DESCRIPTION OF THE INVENTION

The present invention is directed towards the novel manufacturing process of Escitalopram of Formula I.

The Diol compound (VI), used as a starting material in the process of the present invention, is synthesized from 5-cyanophthalide by two successive Grignard reactions with 4-fluorophenylmagnesium bromide and 3-(N,N-dimethylamino)propylmagnesium chloride.

According to one embodiment of the present invention, oxalate salt of (±)-4-[4-(dimethylamino)-1-(4-fluorophenyl)-1-hydroxybutyl]-3-(hydroxymethyl)benzonitrile [(±)-Diol oxalate] (VIa) is prepared by treating Diol compound (VI) with oxalic acid dihydrate in an alcohol solvent selected from methanol, ethanol, isopropanol, butanol, isobutanol etc., and preferably ethanol. The oxalate salt of Diol compound (VIa) is isolated by conventional methods with at least 99.5% HPLC purity and melting range 168-171° C.

In another embodiment of the present invention, (±)-Diol oxalate (VIa) is neutralized by treating with an organic or inorganic base, preferably inorganic base in an aqueous organic solvent, selected from ethyl acetate, toluene, methylene chloride, ethylene dichloride, cyclohexane, and preferably toluene. The inorganic base is selected from sodium hydroxide, potassium hydroxide and aqueous ammonia. The purified Diol thus obtained is treated with optically active acid, selected from dibenzoyltartaric acid, Di-p-toluoyltartaric acid, 10-camphorsulfonic acid and the like, in an organic solvent to resolve Diol enantiomers to obtain (S)-(−)-4-[4-(dimethylamino)-1-(4-fluorophenyl)-1-hydroxybutyl]-3-(hydroxymethyl)benzonitrile. Preferably Di-p-toluoyl-D-tartaric acid is used to obtain (S)-Enantiomer of Diol (VII) having HPLC chiral purity of more than 99.5%.

The (S)-(−)-Diol (VII) is cyclized by using a sulfonyl halide, selected from alkylsulfonyl halide such as methanesulfonyl chloride, ethanesulfonyl chloride, p-toluenesulfonyl chloride etc., and preferably methanesulfonyl chloride, and in presence of a base selected from organic or inorganic base, preferably organic base selected from triethylamine, diethylamine, isopropylamine, diisopropylamine, N,N-diisopropylethylamine etc., and preferably triethylamine. The cyclized product thus obtained is dissolved in an organic solvent selected from acetone, acetonitrile, ethanol, methanol, isopropanol, tetrahydrofuran, toluene, cyclohexane, isopropyl ether etc., and preferably in acetone and is treated with oxalic acid dihydrate to obtain Escitalopram oxalate, which is isolated and dried by conventional methods.

This process of the present invention provides Escitalopram oxalate with HPLC purity more than 99.8%.

The details of the process of the invention are provided in the Examples given below which are provided by way of illustration only and therefore should not be construed to limit the scope of the invention

EXAMPLE 1

Preparation of (±)-4-[4-Dimethylamino)-1-(4-fluorophenyl)-1-Hydroxybutyl]-3-(Hydroxymethyl)-Benzonitrile, Oxalate [(±)-Diol Oxalate Salt]

(±)-Diol compound (VI) (12 g, 0.035 mol) and oxalic acid dihydrate (4.64 g, 0.0368, 1.05 mol) were added to methanol (36 ml) and heated the contents to 55-60° C. to obtain a clear solution. The obtained solution was cooled to 25-30° C. and stirred for 3 h to complete the crystallization. Product was filtered and thereafter, dried at 50-60° C. under reduced pressure to yield 11 g of diol oxalate salt (VIa) with HPLC purity 99.93%.

EXAMPLE 2

Preparation of (±)-4-[4-Dimethylamino)-1-(4-Fluorophenyl)-1-Hydroxybutyl]-3-(Hydroxymethyl)-Benzonitrile, Oxalate [(±)-Diol Oxalate Salt]

(±)-Diol compound (VI) (360 g, 1.05 mol) was dissolved in ethanol (1400 ml) and heated to 50-55° C. to obtain a clear solution. Oxalic acid dihydrate (164.40 g, 1.3 mol) was added slowly and cooled the obtained solution to 15-20° C. and stirred for 4 hrs to complete the crystallization. Product formed was filtered and dried at 50-60° C. under vacuum to yield 360 g of Diol oxalate salt (VIa), with HPLC purity of 99.95%. (Melting Range: 168-171° C.)

$^1$H NMR (DMSO-$d_6$) δ ppm:

7.89-7.09 (m, 7H), 5.54 (d. 1H), 4.03 (d, 1H), 2.98-2.94 (m, 2H), 2.63 (s, 6H), 2.32-2.15 m, 2H), 1.6-1.3 (m, 2H)

IR (KBr, cm$^{-1}$):

3230, 3064, 2957, 2889, 2700, 2519, 2475, 2273, 2023, 1770, 1716, 651, 1602, 1560, 1544, 1505, 1487, 1441, 1412, 1397, 1363, 1299, 1241, 1215, 1190, 1157, 1106, 1088, 1041, 1024, 1006.

EXAMPLE 3

Preparation of (±)-4-[4-Dimethylamino)-1-(4-Fluorophenyl)-1-Hydroxybutyl]-3-(Hydroxymethyl)-Benzonitrile, Oxalate [(±)-Diol Oxalate Salt]

(±)-Diol compound (VI) (7 g, 0.0205 mol) and oxalic acid dihydrate (2.83 g, 0.0225 ml) were added to isopropyl alcohol (77 ml) and heated the contents to 75-80° C. to obtain a clear solution. The obtained solution was cooled to 10-15° C. and stirred for 2 h to complete the crystallization. The product was filtered, and thereafter dried at 50-60° C. under reduced pressure for 6 h to give 8.6 g of diol oxalate salt (VIa), with HPLC purity of 99.94%.

EXAMPLE 4

(±)-Diol compound (VI) (7 g, 0.0205 mol) and oxalic acid dihydrate (2.96 g, 0.0235 mol) were added to n-butanol (77 ml) and the contents were heated to 80-85° C. to obtain a clear solution. Obtained solution was cooled slowly to 15-20° C. and stirred for 3 h to complete the crystallization. The product formed was filtered and washed with n-butanol (2×7 ml). Thereafter, product was dried at 50-60° C. under reduced pressure to give 8.5 g of diol oxalate salt (VIa), with HPLC purity of 99.93%.

EXAMPLE 5

Preparation of Escitalopram Oxalate

Step-1:
Preparation of (S)-(−)-4-[4-(Dimethylamino)-1-(4-Fluorophenyl)-1-Hydroxybutyl]-3-(Hydroxymethyl)-Benzonitrile, Hemi (+)-Di-P-Toluoyl-D-Tartaric Acid Salt [(S)-(−)-Diol Dptta Salt]

(±)-Diol oxalate (VIa) (225 g, 0.52 mol) was suspended in a mixture of DM water (2250 ml) and toluene (2250 ml) at 30-35° C. and pH was raised to 9.8 using aqueous ammonia solution. The organic layer was separated, was washed with DM water and concentrated at 50-55° C. under reduced pressure. The obtained residue was dissolved in isopropyl alcohol (1125 ml) at 50-55° C. (+)-Di-p-toluoyl-D-tartaric acid (105 g, 0.27 mol) was added and slowly cooled to 25-30° C. and stirred for 10 h. The crystals formed in the reaction mixture were filtered and washed with isopropyl alcohol (2×110 ml) to obtain~180 g product (chiral purity:>96%).

The above salt was suspended in isopropyl alcohol (1500 ml) and heated to 80° C. to obtain a clear solution. The resulting solution was cooled to 20-25° C. and stirred for 1 hr. The solids were filtered and washed with isopropyl alcohol (2×50 ml) and thereafter dried to yield 102 g of the above salt. Chiral purity (by HPLC): 99.94%; [α]$_D$: +8.0 (c=1, in methanol, on anhydrous basis).

Step-2:
Preparation of Escitalopram Oxalate (S)-(−)-Diol DPTTA salt (80 g, 0.075 mol) was suspended in a mixture of DM water (800 ml) and methylene chloride (800 ml) at 20-25° C. The pH of the resulting solution was adjusted to 10.1 using aqueous sodium hydroxide solution at 20-25° C. Organic layer was separated and washed with DM water (1×300 ml). Thereafter, the organic layer was partially concentrated at atmospheric pressure at 35-39° C. and the resulting concentrated mass was cooled to −5° C. to −10° C.

Triethylamine (42.30 g, 0.41 mol) was added under nitrogen atmosphere, followed by addition of methanesulfonyl chloride (18 g, 0.16 mol) slowly at −5° C. to −10° C. over a period of 3 h and progress of the reaction was monitored by qualitative HPLC analysis. After completion of the cyclization, the reaction mass was washed with 0.5% w/w aqueous sodium hydroxide solution followed by DM water at 0-10° C. Methylene chloride was distilled from reaction mass at 20-30° C. in vacuum to get Escitalopram base. Chiral purity: 99.12%; Chromatographic purity (by HPLC): 98.42%.

The oxalate salt of the above base was obtained by treating it with oxalic acid dihydrate in acetone. Chiral purity: 99.01%; Chromatographic purity: 99.85%; [α]$_D$: +13.4 (c=1, in methanol, on anhydrous basis).

We claim:
1. A process for the preparation of Escitalopram of Formula I,

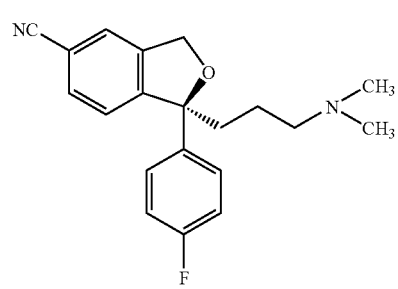

I which comprises,
(i) reacting the diol compound (VI),

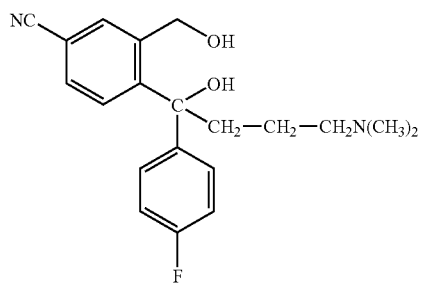

with oxalic acid in an organic solvent to get crystalline oxalate salt of (±)-4-[4-(dimethylamino)-1-(4-fluorophenyl)-1-hydroxybutyl]-3-(hydroxymethyl)-benzonitrile [(±)-Diol oxalate] (VIa),

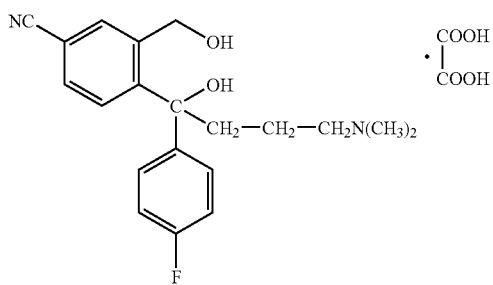

(ii) isolating the crystalline Diol oxalate (VIa) by filtration and neutralizing the oxalate salt to get pure diol compound (VI),
(iii) separating the enantiomers from the pure Diol compound (VI) with an optically active acid precipitant to obtain (S)-(−)-4-[4-(dimethylamino)-1-(4-fluorophenyl)-1-hydroxybutyl]-3-(hydroxymethyl)benzonitrile (VII),

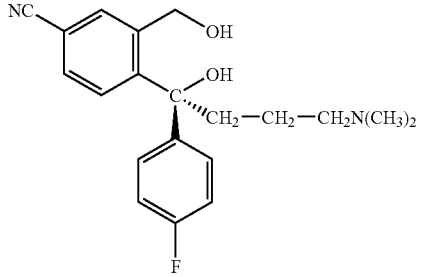

(iv) cyclizing the (S)-(−)-Diol (VII) in an organic solvent in the presence of sulfonyl halide and a base to produce Escitalopram (I).

2. The process as claimed in claim 1, wherein the organic solvent used in step-(i) is selected from methanol, ethanol, isopropanol, n-butanol, isobutanol.

3. The process as claimed in claim 1, wherein the neutralization in step-(ii) is carried out using inorganic base, selected from aqueous ammonia, aqueous sodium hydroxide or aqueous potassium hydroxide.

4. The process as claimed in claim-1, wherein the optically active precipitant is Di-p-toluoyl-D-tartaric acid.

5. The process as claimed in claim 1, wherein the solvent is used for cyclization is selected from methylene chloride, toluene, cyclohexane, tetrahydrofuran, acetonitrile.

6. The process as claimed in claim 1, wherein the sulfonyl halide used for cyclization step is methanesulfonyl chloride.

7. The process as claimed in claim 1, wherein the base used in cyclization step is an organic or an inorganic base and preferably an organic base.

8. The process as claimed in claim 7, the organic base is triethylamine.

* * * * *